United States Patent [19]

Chen

[11] Patent Number: 5,273,539

[45] Date of Patent: Dec. 28, 1993

[54] AUTOMATICALLY BLOCKED SAFETY SYRINGE ADAPTED FOR INTRAVENOUS INJECTION

[76] Inventor: Long-Hsiung Chen, c/o Hung Hsing Patent Service Center, P.O. Box 55-1670, Taipei (10477), Taiwan

[21] Appl. No.: 24,211

[22] Filed: Mar. 1, 1993

[51] Int. Cl.$^5$ .............................................. A61M 5/00
[52] U.S. Cl. .................................... 604/110; 604/195
[58] Field of Search ............... 604/110, 195, 187, 220, 604/218, 228

[56] References Cited

U.S. PATENT DOCUMENTS

| | | | |
|---|---|---|---|
| 4,804,370 | 2/1989 | Haber et al. | 604/110 |
| 5,104,378 | 4/1992 | Haber et al. | 604/110 |
| 5,171,300 | 12/1992 | Blake, III et al. | 604/195 X |

*Primary Examiner*—John D. Yasko

[57] ABSTRACT

A safety syringe includes a hollow needle for intravenous injection use eccentrically mounted in a syringe with said needle preliminarily held in a rigid blocking bulb generally conical shaped or truncated-cone shaped having an elongate stem portion protruding rearwardly from the bulb embedded in a rear bulb socket perpendicularly formed in a flexible plug inserted in a front porton of the syringe having a needle head portion formed on a rear portion of the needle, and a plunger slidably held in the syringe for boosting a liquid medicine in the syringe to be injected into a patient through the hollow needle having an annular groove annularly recessed in the plunger to be engageable with the needle head portion to drive and move the rigid blocking bulb frontwardly from the rear bulb socket into a front bulb socket which is normally inclinedly formed in the flexible plug and will be operatively biased perpendicularly in the plug when almost exhausting the liquid in the syringe when finishing the injection, whereby upon a retraction of the plunger and the needle coupled to the plunger rearwardly into the syringe, the elongate stem portion of the rigid bulb will be greatly obliquely biased in a larger angle by the front bulb socket of the plug to be much inclinedly positioned for efficiently blocking an outward protruding of the needle retracted in the syringe for really preventing an injury or infectious contamination to the surroundings as caused by the needle.

5 Claims, 5 Drawing Sheets

AUTOMATICALLY BLOCKED SAFETY SYRINGE ADAPTED FOR INTRAVENOUS INJECTION

BACKGROUND OF THE INVENTION

An invention patent application for a safety syringe, filed by the same inventor of this application on Nov. 30, 1992 given a Ser. No. of 07/983,144, includes: a hollow needle (2) preliminarily held in a rigid blocking disk (4) embedded in a rear disk socket (135) perpendicularly formed in a flexible plug (13) inserted in a front portion of the syringe (1) for injection use having a needle head portion (23) formed on a rear portion of the needle (2), and a plunger (31) slidably held in the syringe (1) for boosting a liquid medicine in the syringe to be injected into a patient through the hollow needle (2) having a needle-head socket (32) recessed in the plunger (31) to be engageable with the needle head portion (23) for pushing the needle head portion of the needle (2) frontwardly to drive the rigid blocking disk (4) frontwardly to engage the blocking disk (4) into a front disk socket (137) which is normally inclinedly formed in the flexible plug (13), whereby upon a retraction of the plunger (31) and the needle (2) with the needle head portion (23) received in and coupled to the plunger (31) into the syringe (1) to disengage the needle (2) from the rigid disk (4), the flexible plug (13) will restore the front socket (137) and the rigid disk (4) embedded in the front socket (137) to be inclinedly positioned in the plug (13), thereby blocking an outward protruding of the needle (2) retracted in the syringe (1) for preventing its injury or infectious contamination to the surroundings.

However, the blocking disk member 4 of this earlier application is made as a shallow disk, the central through hole 41 of the block disk member 4 can only be biased for a small oblique angle, which may still be accidentally inserted by an outwardly protruding of the needle (2) already retracted in the syringe (1) to lose its safety meaning.

Meanwhile, the hollow needle (2) of such a safety syringe is normally provided in a central portion of the syringe means (1), which is suitable for hypodermic or intramuscular injection. However, if such a syringe is used for intravenous or intravascular injection of larger quantity of liquid medicine filled in the syringe cylinder (11) such as a volume of 30 cc, 50 cc, or 100 cc of the liquid medicine. The needle (2) should be eccentrically formed in the syringe cylinder for an ergonomic injection by a nurse or a doctor since the needle and the syringe cylinder can be held in a direction parallel and close to the patient's vein or blood vessels.

If the inventor's earlier application (U.S. patent application Ser. No. 07/983,144) is inferentially used for an intravenous injection of larger injection quantity, the needle (2) should be eccentrically mounted in the syringe cylinder (11). Meanwhile, the single needle-head socket (32) should also be eccentrically moved in order to engage with the needle head portion (23) of the needle (2). It will be very difficult and inconvenient for matching a needle head portion (23) of an eccentrically-positioned needle (2) with the single needle-head socket (32).

It is therefore expected to disclose a syringe for improving the drawbacks of the applicant's earlier application in order that a used needle can be easily retractable into the syringe in a safer way for preventing an outward protruding of the retracted needle.

SUMMARY OF THE INVENTION

The object of the present invention is to provide a safety syringe including: an annular groove annularly recessed in a front surface of a plunger slidably held in the syringe to be engageable with a needle head portion formed on a rear portion of a hollow needle which is eccentrically mounted in a front portion of the syringe for intravenous injection uses, with the annular groove having a longitudinal section formed as an elliptical needle-head socket engageable with the needle head portion for retracting the plunger and the needle into the syringe, wherein the retracted needle will be automatically blocked for preventing an outward protrusion of the needle.

Substantially, the present invention provides a safety syringe including the hollow needle preliminarily held in a rigid blocking bulb generally conical shaped or truncated-cone shaped having an elongate stem portion protruding rearwardly from the bulb first embedded in a rear bulb socket perpendicularly formed in a flexible plug inserted in a front porton of the syringe having the needle head portion formed on a rear portion of the needle, and the plunger when coupled with the needle head portion will operatively drive and move the rigid blocking bulb frontwardly when performing the injection into a front bulb socket which is normally inclinedly formed in the flexible plug, whereby upon a retraction of the plunger coupled with the needle rearwardly into the syringe, the elongate stem portion of the rigid bulb will be greatly obliquely biased in a larger angle by the front bulb socket of the plug to be much inclinedly positioned for efficiently blocking an outward protruding of the needle retracted in the syringe for really preventing an injury or infectious contamination to the surroundings as caused by the needle.

DETAILED DESCRIPTION

Figure 2:
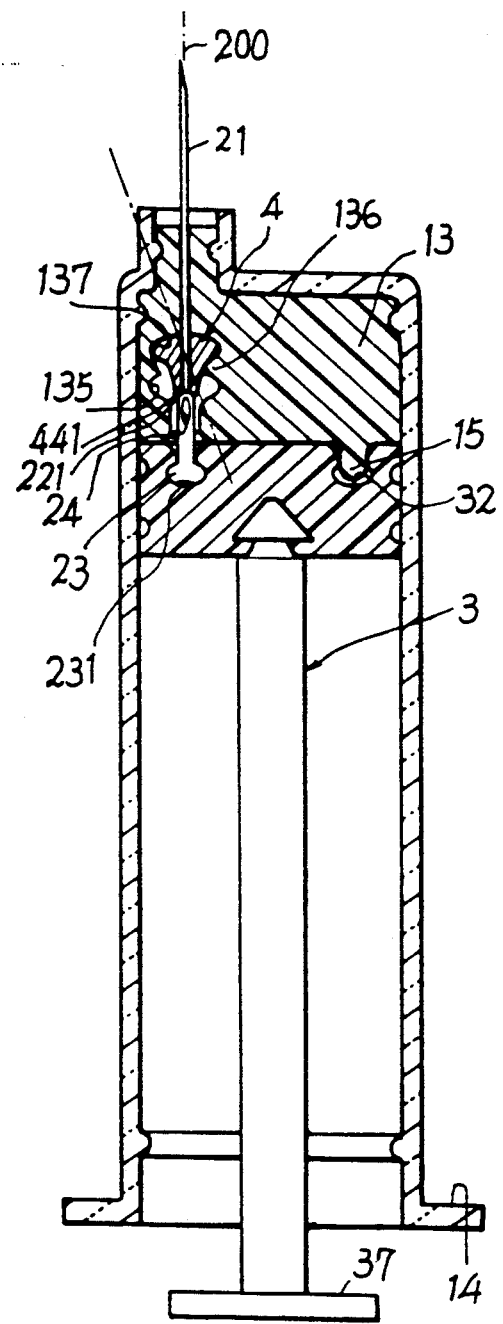
FIG. 2 is an illustration showing the present invention when finishing the injection.

As shown in FIGS. 1-7, the present invention comprises: a syringe means 1, a hollow needle 2 mounted in an eccentric front portion of the syringe means 1, a plunger means 3, and a rigid blocking bulb 4 movably held in the syringe means 1.

The syringe means 1 includes: a syringe cylinder 11 having a hollow bore portion 10 defined in the syringe cylinder 11 and a syringe axis 100 longitudinally existing in a central portion of the syringe cylinder 11 having a plurality of annular extension rings 111 circumferentially formed in an inner front portion inside the cylinder 11, a sleeve portion 12 protruded and contracted frontwardly from the syringe cylinder 11 and formed in an eccentric front portion of the syringe cylinder 11 having a needle port 121 formed in an front opening of the sleeve portion 12, a flexible plug 13 perferably made of soft, flexible elastomer materials inserted in the front portion inside the cylinder 11 having a plug tip portion 131 embedded in the sleeve portion 12 and a plug shoulder portion 133 embedded in a front portion of the cylinder 11 connected with the plug tip portion 131 and a tunnel 130 formed in the plug 13 communicating the needle port 121 for inserting the needle portion 21 therethrough, a plurality of annular grooves 132 circumferentially formed on a cylindrical side wall portion of the plug 13 engageable with the extension rings 122, 111 respectively formed in the sleeve portion 12 and the cylinder 11 for fixing the plug 13 in the cylinder 11, a first bulb socket 135 perpendicularly formed in a rear eccentric portion of the plug 13 and communicating with a plug guiding port 134 tapered frontwardly from a plug rear surface 133a, and a second bulb socket 137 normally inclinedly formed in a front eccentric portion of the plug 13 communicating with the first bulb socket 135 through a throat portion 136 formed between the two bulb sockets 135, 137, of which either bulb socket 135 or 137 is operatively engageable with the rigid blocking bulb 4, a syringe handle 14 formed on a rear end portion of the cylinder 11, and a liquid-repelling extension 15 arcuately or concentrically formed on the plug rear surface 133a of the plug 13 with a flat surface portion 151 disposed around the tunnel 13 recessed in the liquid-repelling extension 15 and coplanar to the plug rear surface 133a.

Figure 1:
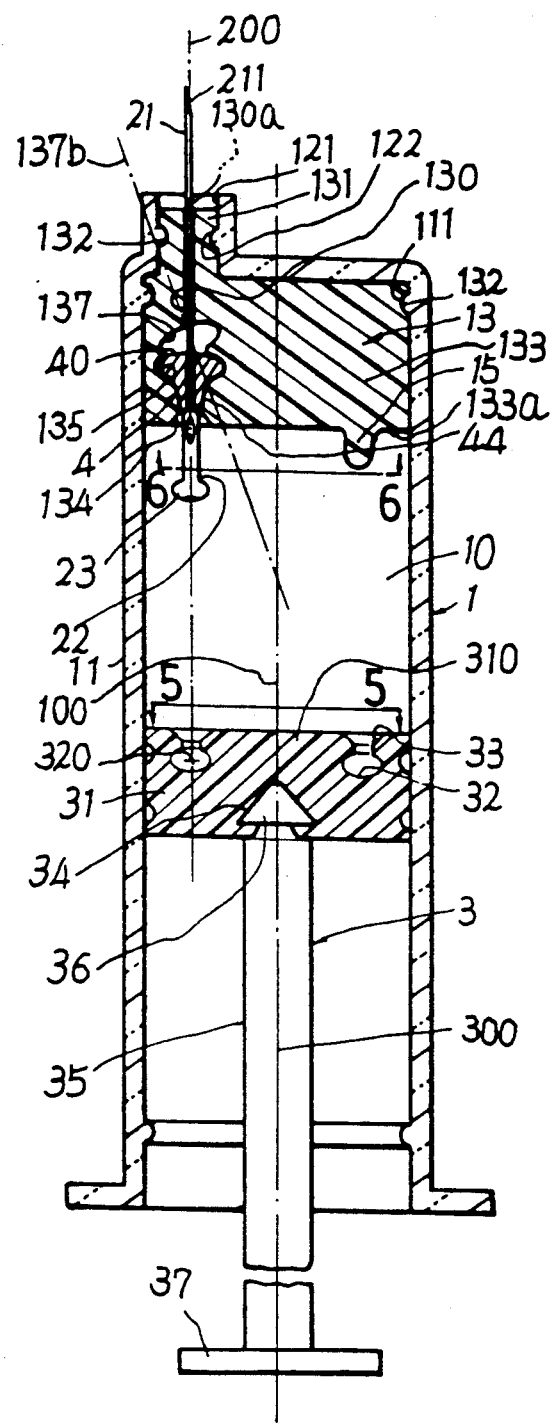
FIG. 1 is an illustration showing the present invention before injection.
Figure 1A:
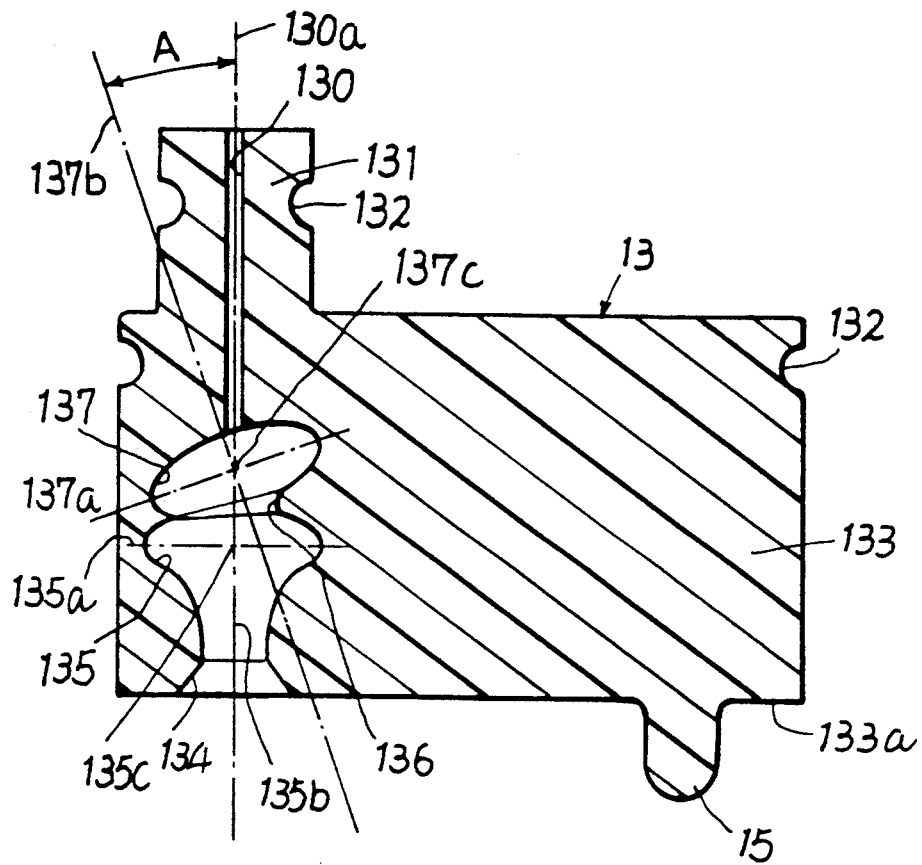
FIG. 1a is a sectional drawing of a flexible plug of the present invention.

As shown in FIG. 1a, the flexible plug 13 includes the first bulb socket 135 having a longitudinal section generally elliptic shaped and having a first socket center 135c intersected by a first transverse axis 135a, and a first conjugate axis 135b which is normally aligned with a tunnel axis 130a of the tunnel 130, thereby orienting the first transverse axis 135a to be normally perpendicular to the tunnel axis 130a. The tunnel axis 130a is parallel to the syringe axis 100 of the syringe means 1.

The second bulb socket 137 has a longitudinal section generally elliptic shaped and having a second socket center 137c intersected by a second transverse axis 137a, and a second conjugate axis 137b which defines an acute angle A with the tunnel axis 130a and is unaligned with the tunnel axis 130a, thereby normally orienting the second transverse axis 137a inclinedly in the plug 13. The sockets 135, 137 each may have a longitudinal section of elliptical shape, triangular shape or other suitable shapes; or may be formed as truncated-cone shape.

The rigid blocking bulb 4 is made of rigid plastic or other rigid, hard materials insertable in either socket 135 or 137 in the soft flexible plug 13, and is preferably formed as a conical or truncated-cone shape including a bulb base portion 40 and an elongate stem portion 44 tapered or contracted rearwardly from the bulb base portion 40 to be engageable with either bulb socket 135 or 137 in the plug 13 with the bulb base portion 40 having a longitudinally section of elliptical shape, having a through hole 41 defining a bulb axis 400 longitudinally formed in a central portion through the blocking bulb 4 for passing the needle portion 21 of the hollow needle 2 therethrough, a bulb base center 420 intersected by a transverse bulb axis 43 and a conjugate bulb axis 42 existing in a longitudinal center line of the base portion 40 normally aligned with the tunnel axis 130a and a needle axis 200 of the needle 2 when the bulb 4 is normally held in the first bulb socket 135 in the plug 13 and the hollow needle 2 is longitudinally held in the plug 13 ready for injecting a liquid medicine filled in the bore portion 10 of the syringe cylinder 11 as shown in FIG. 1.

A rear bulb surface 441 of the bulb stem portion 44 can be matched with a shoulder portion 221 formed in a front surface of a needle shank portion 22 of the needle 2 to be forwardly driven by the needle shank portion 22 and needle head portion 23 from FIG. 1 to FIG. 2.

The rigid blocking bulb 4 as held on the needle portion 21 to be limited by the shank portion 22 (shoulder portion 221) of the needle is operatively thrusted from the first bulb socket 135 into the second bulb socket 137 through the throat portion 136 between the two bulb sockets 135, 137, with the throat portion 136 defining a diameter smaller than a length of the transverse axis 135a or 137a of any said bulb socket 135, 137.

The hollow needle 2 includes: a needle portion 21 protruding outwardly through the sleeve portion 12 of the syringe means 1 having a tip end 211 formed on an outermost end of the needle, a shank portion 22 connected with the needle portion 21 with a shoulder portion 221 normally contacted with the rear bulb surface 441 of the stem portion 44 of the blocking bulb 4 with a rear end portion of the needle portion 21 inserted in the bulb 4 normally held in the plug 13 for normal injection of the syringe means 1, a needle head portion 23 formed on a rear portion of the shank portion 22 normally protruding rearwardly beyond a plug rear surface 133a to be engageable with an annular groove 32 formed in the plunger means 3 having an injection hole 231 formed in the needle head portion 23 communicating with a needle hole 20 formed through the hollow needle 2, a needle axis 200 longitudinally existing in a central portion of the needle 2 normally aligned with the tunnel axis 130a and parallel to the syringe axis 100 when held in the plug 13 for normal injection purpose as shown in FIG. 1, and at least a venting slot 24 formed in the shank portion 22 adjacent to the needle head portion 23 for venting air outwardly through the needle hole 20 of the hollow needle.

The needle head portion 23 of the hollow needle 2 may be formed as elliptic shape to be engaged with the annular groove 32 having a longitudinal section of elliptical shape formed in the plunger means 3, but not limited in this invention.

The plunger means 3 includes: a plunger 31 reciprocatively held in the syringe cylinder 11, the annular groove 32 annularly recessed in a plunger front surface 310 of the plunger 31 operatively engageable with the needle head portion 23 having a plunger guiding port 33 tapered rearwardly from the plunger front surface 310 for communicating with the annular groove 32 for engageably receiving and coupling the needle head portion 23 when finishing the injection for a retraction of the needle 2 as coupled to the plunger 31 into the syringe cylinder 11, a plunger rod 35 having a coupling member 36 engaged with a rear recess 34 formed in the plunger 31 for coupling the plunger 31 on the rod 35 and a plunger handle 37 for pushing the plunger 31 for boosting liquid medicine in the syringe cylinder 11 for injection use. The annular groove 32 has a longitudinal section of elliptical socket defining a socket center perpendicular to a plunger axis 300 which is aligned with the syringe axis 100 and longitudinally formed in a center line of the plunger means, and projectively aligned with a needle head center 230 of the needle head portion 23 for a snug engagement of the needle head portion 23 with the elliptical socket of the annular groove 32 of the plunger 31 for coupling the needle 2 to the plunger means 3 which is operatively pushed frontwardly for movably driving the rigid blocking bulb 4 from a first bulb socket 135 to a second bulb socket 137 when finishing the injection (FIG. 2) and is then retracted to pull the needle 2 coupled on the plunger 31 to be stored into the syringe cylinder 11, whereby the rigid blocking bulb 4 will then be automatically restored by the flexible plug 13 to be inclinedly positioned in the plug 13 and the central through hole 41 of the blocking bulb 4 is then unaligned with the tunnel axis 130a as shown in FIG. 3 for blocking an outward protrusion of the retracted needle portion 21 for preventing a sting injury or infectious contamination by the needle 2.

The liquid-repelling extension 15 concentrically formed in a rear surface 133a of the plug 13 inserted in a front portion of the syringe cylinder 11 has the flat surface portion 151 recessed in the liquid-repelling extension 15 and coplanar to the rear surface 133a of the plug 13 for receiving the needle 2 within the recessed flat surface portion 151, with the liquid-repelling extension 15 having a longitudinal section of arcuate or semicircular shape and engageable with the annular groove 32 recessed in the plunger 31, thereby squeezing the liquid medicine outwardly as filled into the annular groove 32 when moving and pumping the plunger 31 towards the plug 13 for almost finishing the injection operation for saving any medicine and preventing loss of medicine even a small volume filled in the groove 32.

Figure 3:
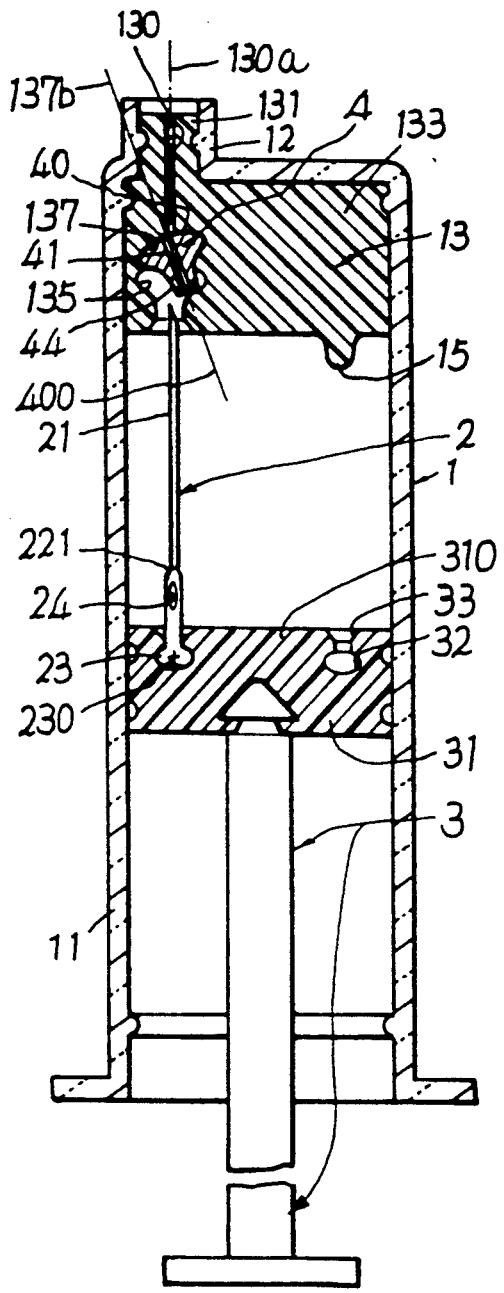
FIG. 3 shows the present invention having a needle retracted in a syringe.
Figure 5:
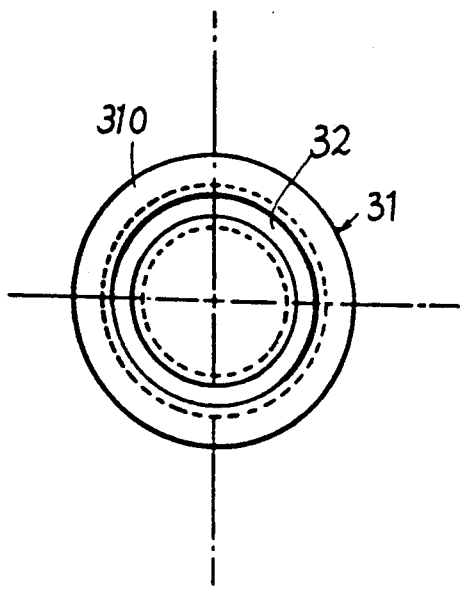
FIG. 5 is a top view of a plunger when viewed from 5—5 direction of FIG. 1.
Figure 6:
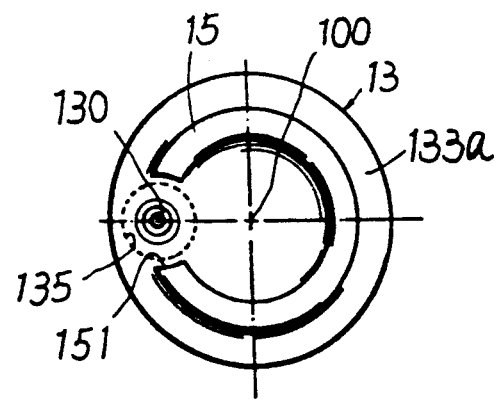
FIG. 6 is a bottom view of the plug in the syringe when viewed from 6—6 direction of FIG. 1.

The liquid-repelling extension 15 has the longitudinal section of arcuate shape to be slightly smaller than the elliptical socket of the annular groove 32 for an easy decoupling of the plunger 31 from the plug 13 when retracting the needle device 2 into the syringe cylinder 11 (FIG. 2 to FIG. 3).

Figure 4:
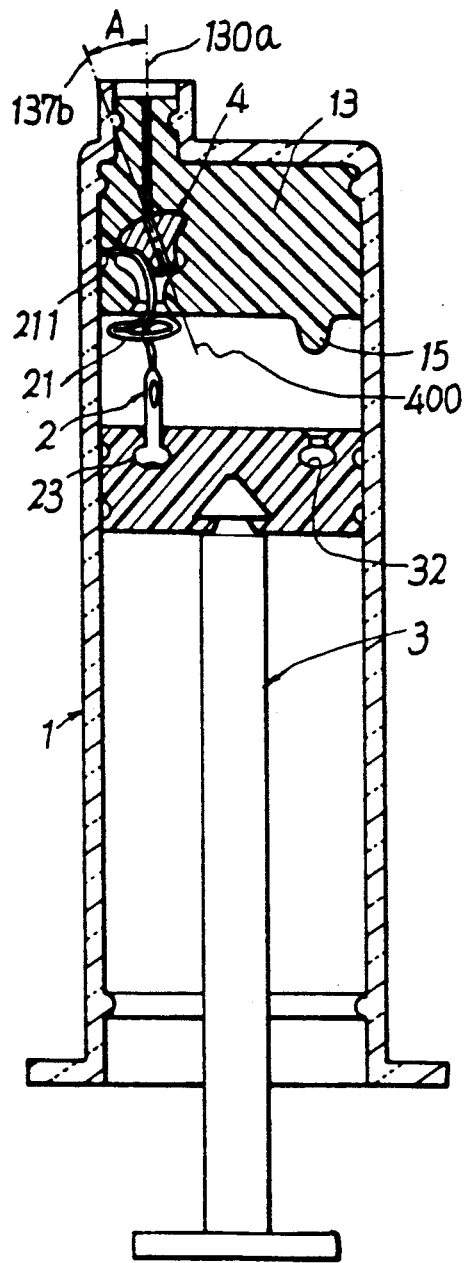
FIG. 4 shows a blocking effect for retarding an outwardly protruding needle in accordance with the present invention.

As shown in FIG. 4, a further outward protrusion of the needle 2 will be automatically blocked by the blocking bulb 4 by bending, deforming or poking the needle tip end 211 into the plug 3 to be obstructed by the syringe cylinder 11 (FIG. 4) which can not be pushed outwardly from the syringe cylinder 11 for a better safety and hygienic protection.

After the retraction of the needle 2 coupled to the plunger 31 into the syringe cylinder 11 as shown in FIG. 3, the flexible plug 13 will be automatically restored by its self elasticity to restore the second socket 137, from its flattened state (blocking bulb 4 perpendicular to the axis 130a) as pressurized by the plunger means 3 as shown in FIG. 2, to be an inclined situation wherein the rigid blocking bulb 4 will be restored to be inclinedly positioned (FIG. 3), thereby blocking the unexpected outwardly protrusion of a retracted needle 2 as shown in FIG. 4.

Figure 7:
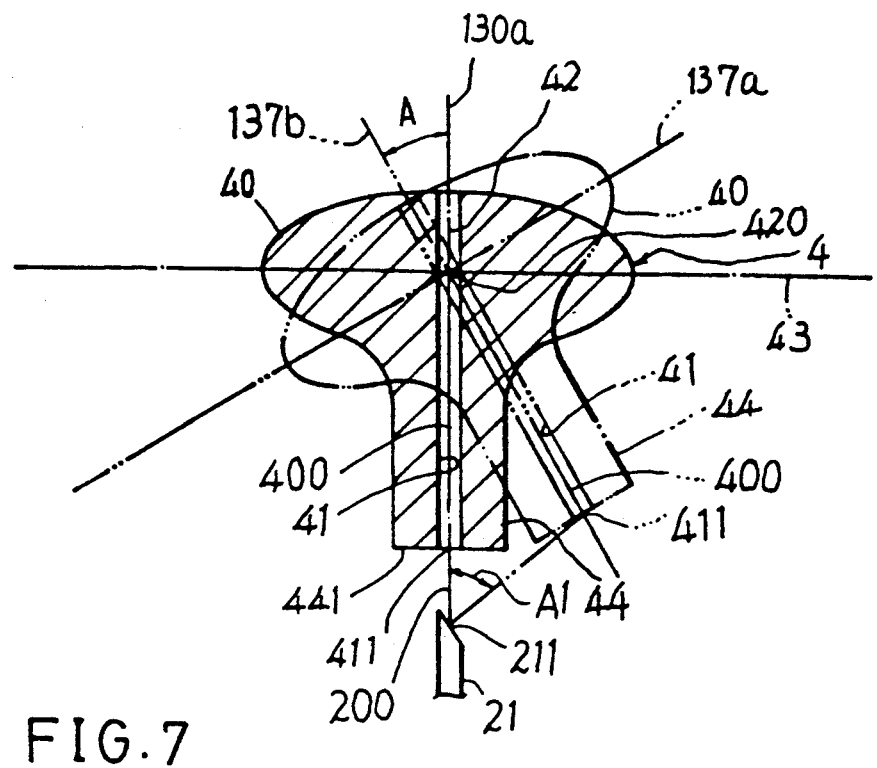
FIG. 7 shows a rigid blocking bulb of the present invention.
Figure 8:
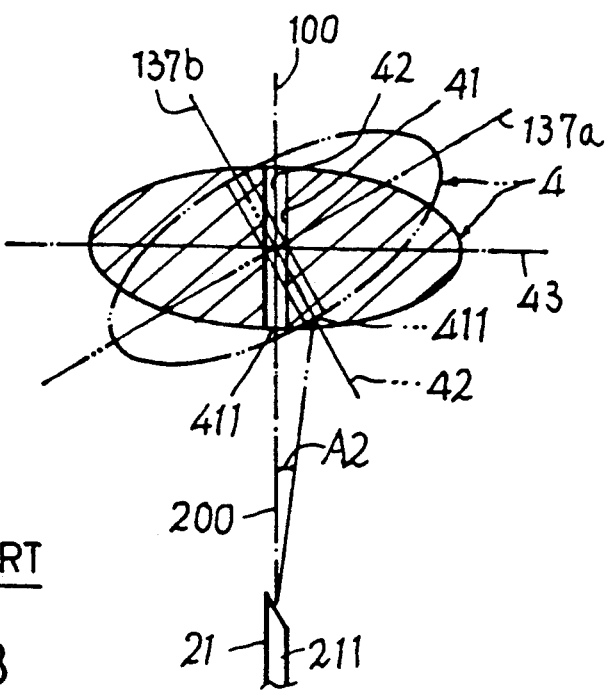
FIG. 8 shows a rigid blocking disk member of the prior art.

As shown in FIG. 7, the bulb 4 of this application includes the elongate stem portion 44 protruding rearwardly from the bulb base portion 40 to thereby greatly increase a deviation angle A1, wider than a smaller angle A2 as effected by the "shallow" blocking disk member of the prior art (U.S. patent application Ser. No. 07/983,144) as shown in FIG. 8, so that it will be more difficult to protrude the retracted needle tip end portion 211 of this application outwardly through an "inlet port" or rear port 411 of the central through hole 41 of the blocking bulb 4, to be safer than the prior art as shown in FIG. 8 since the deviation angle A1 of this application is much increased than that A2 of the prior art.

Meanwhile, the stem portion 44 of the bulb of this application can be easily grasped for a smoothly mounting of the bulb 4 with the needle 2 to be embedded into the socket 135 for an easier assembly and production of this application than the prior art.

I claim:

1. A safety syringe comprising:

a syringe means including: a sleeve portion eccentrically formed in a front side portion in a syringe cylinder, a flexible plug inserted in a front portion inside the syringe cylinder of said syringe means having a tunnel eccentrically formed through the plug to define a tunnel axis aligned with a longitudinal central line of said sleeve portion, said tunnel axis being parallel to a syringe axis longitudinally existing in a central portion in said syringe means, said flexible plug having a first bulb socket formed in a rear portion in said plug normally perpendicular to said tunnel axis, and a second bulb socket formed in a front portion in said plug and communicating with said first socket and normally inclinedly positioned in said plug;

a rigid blocking bulb generally conical shaped, including a bulb base portion and an elongate stem portion tapered rearwardly from said bulb base portion having a central through hole longitudinally formed through said bulb, normally engageably held in said first bulb socket of said plug and operatively moved into said second bulb socket to be engageable with said second bulb socket; and a hollow needle normally held in said rigid blocking bulb and in said plug defining a needle axis normally aligned with said tunnel axis with said needle eccentrically mounted in said syringe means adapted for an intravenous injection, and operatively thrusted frontwardly as urged by a plunger of a plunger means reciprocatively held in said syringe means to be moved frontwardly from said first bulb socket towards said second bulb socket when finishing an injection, said needle being operatively coupled to said plunger of said plunger means when finishing the injection by engaging a needle head portion formed on a rear end portion of said hollow needle with an annular groove annularly recessed in the plunger of said plunger means with said needle axis of said needle retracted in said syringe means being projectively aligned with said tunnel axis formed in said plug and said sleeve portion, whereby upon a retraction of said needle into said syringe cylinder, said flexible plug will automatically restore said second bulb socket to inclinedly orient said rigid blocking bulb to projectively unalign the central through hole of said bulb from said needle axis of said hollow needle coupled to said plunger means to greatly deviate a positioning of a rear port of the through hole, formed in a rear stem surface of said stem portion of said bulb, from the tunnel axis of the tunnel and the needle axis of the needle for effectively preventing an outward protrusion of the needle as retracted in said syringe cylinder.

2. A safety syringe according to claim 1, wherein each said first and second bulb socket has a longitudinal section of elliptical shape engageable with an elliptically shaped bulb base portion of said blocking bulb.

3. A safety syringe according to claim 1, wherein each said first and second bulb socket has a longitudinal section of triangular shape, engageable with said blocking bulb generally conical shaped.

4. A safety syringe according to claim 2, wherein said second bulb socket defines a second transverse axis and a second conjugate axis perpendicular to said second transverse axis, with said second conjugate axis of said second bulb socket operatively aligned with a conjugate bulb axis of the elliptically shaped bulb base portion of said blocking bulb having defining a transverse bulb axis perpendicular to said conjugate bulb axis.

5. A safety syringe according to claim 1, wherein said plug in said syringe cylinder includes a liquid-repelling extension concentrically formed in a rear surface of the plug inserted in the front portion of the syringe cylinder having a flat surface portion recessed in the liquid-repelling extension an coplanar to the rear surface of the plug for receiving the needle head portion of the hollow needle within the flat surface portion, with the liquid-repelling extension having a longitudinal section of arcuate shape and engageable with the annular groove recessed in the plunger for operatively squeezing the liquid medicine outwardly as filled into the annular groove when pumping the plunger towards the plug for finishing the injection operatively for saving any medicine filled in the annular groove.

* * * * *